United States Patent [19]
Bromberg et al.

[11] Patent Number: 5,256,854
[45] Date of Patent: Oct. 26, 1993

[54] TUNABLE PLASMA METHOD AND APPARATUS USING RADIO FREQUENCY HEATING AND ELECTRON BEAM IRRADIATION

[75] Inventors: Leslie Bromberg, Sharon; Daniel R. Cohn, Chestnut Hill; William C. Guss, Arlington; Barton G. Lane, Belmont; Donna L. Smatlak, Arlington, all of Mass.

[73] Assignee: Massachusetts Institute of Technology, Cambridge, Mass.

[21] Appl. No.: 629,424

[22] Filed: Dec. 18, 1990

[51] Int. Cl.⁵ ................................................ B23K 9/00
[52] U.S. Cl. .......................... 219/121.52; 219/121.59; 219/121.43; 219/121.21; 110/242; 110/244; 250/492.21
[58] Field of Search ...................... 219/121.43, 121.44, 219/121.4, 121.21, 121.12, 121.35, 121.59; 204/298.36, 298.37; 110/242–244; 156/345; 118/50.1; 250/25, 492.21; 427/34; 315/111.51, 111.21, 111.81

[56] References Cited

U.S. PATENT DOCUMENTS

| | | | |
|---|---|---|---|
| 4,511,593 | 4/1985 | Brandolf | 118/50.1 |
| 4,511,594 | 4/1985 | Yanai et al. | 118/50.1 |
| 4,514,437 | 4/1985 | Nath | 118/50.1 |
| 4,739,170 | 4/1988 | Varga | 250/251 |
| 4,842,704 | 6/1989 | Collins et al. | 204/298.21 |
| 4,851,668 | 7/1989 | Ohno et al. | 250/251 |
| 4,874,459 | 10/1989 | Coldren et al. | 204/298.36 |
| 4,897,579 | 1/1990 | Hull et al. | 315/111.51 |
| 5,098,483 | 3/1992 | Little et al. | 148/4 |

OTHER PUBLICATIONS

Gollands, et al., "Stack Testing of the Mobile Plasma Arc Unit", EPA Hazardous Waste Engineering Research Laboratory, May, 1987.
Frank, Norman W. et al., "Operating and Testing a Combined SO₂ and NOₓ Removal Facility", Environmental Progress, 6, pp. 177–182, (1987).
Kolak, Nicholas P., et al., "Trial Burns—Plasma Arc Technology", Nuclear and Chemical Waste Management, 7, pp. 37–41, (1987).
Hiley, J. et al., "High-Power Selfshielded Electron Processors and Their Application to Stack Gas Treatment", Nuclear Instruments and Methods in Physics Research, B24/25, pp. 985–989, (1987).
Barton, Thomas G., "Mobile Plasma Pyrolysis", Hazardous Waste, 1, pp. 237–247, (1984).
Barton, T. G., et al., "Managing PCB Wastes", Engineering Journal of Canada, 63, pp. 40–42 (1980).
Reed, Thomas B., "Induction-coupled Plasma Torch", Journal of Applied Physics, 32, pp. 821–824, (1961).
Eckert, Hans U., "Induction Plasmas at Low Frequencies", AIAA Journal, 9, pp. 1452–1456, (1971).
Bailin, Lionel J. et al., "Microwave Decomposition of Toxic Vapor Stimulants", Environmental Science & Technology, 9, pp. 254–258, (1975).
Daugherty, Jack D., "Electron Beam Ionized Lasers", Chapter 9 of Principles of Laser Plasmas, George Bekefi, Ed., pp. 369–419.

*Primary Examiner*—Mark H. Paschall
*Attorney, Agent, or Firm*—Choate, Hall & Stewart

[57] ABSTRACT

A method and apparatus for the pyrolytic destruction or synthesis of gases via a highly tunable combination of radio frequency heating and electron beam irradiation is disclosed. The method is appropriate for destroying toxic gases emanating from hazardous wastes and for synthesizing new molecules from the molecules of a gas. The method is also appropriate for creating scavenger gases and hot gases with large enthalpy for use in sterilization procedures, for example. Embodiments are disclosed employing inductive or direct waveguide/cavity coupling of radio frequency power to the gas. In embodiments of the invention, magnetic fields are used to modify the paths of the electrons in the beam to facilitate tuning and improve the energy efficiency of the system. In a two-stage system, solid and/or liquid wastes are first heated in order to vaporize the toxic materials. Then, the gases produced in the first stage are destroyed by the combination of radio frequency heating and electron beam irradiation of the invention.

20 Claims, 6 Drawing Sheets

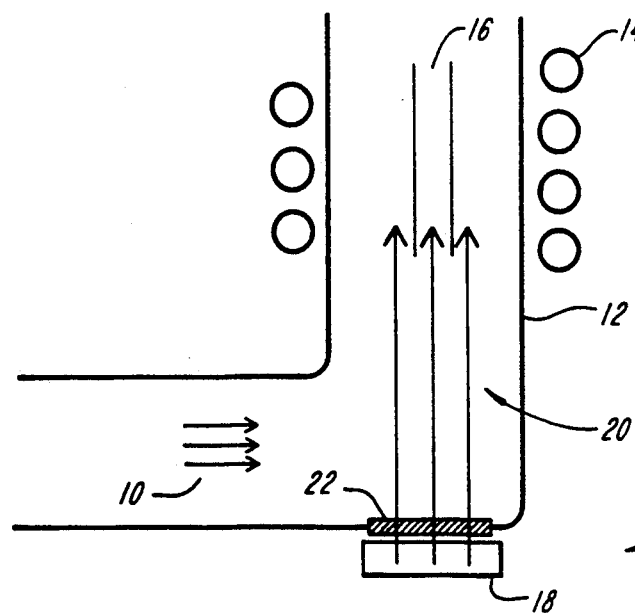
FIG. 3
FIG. 4
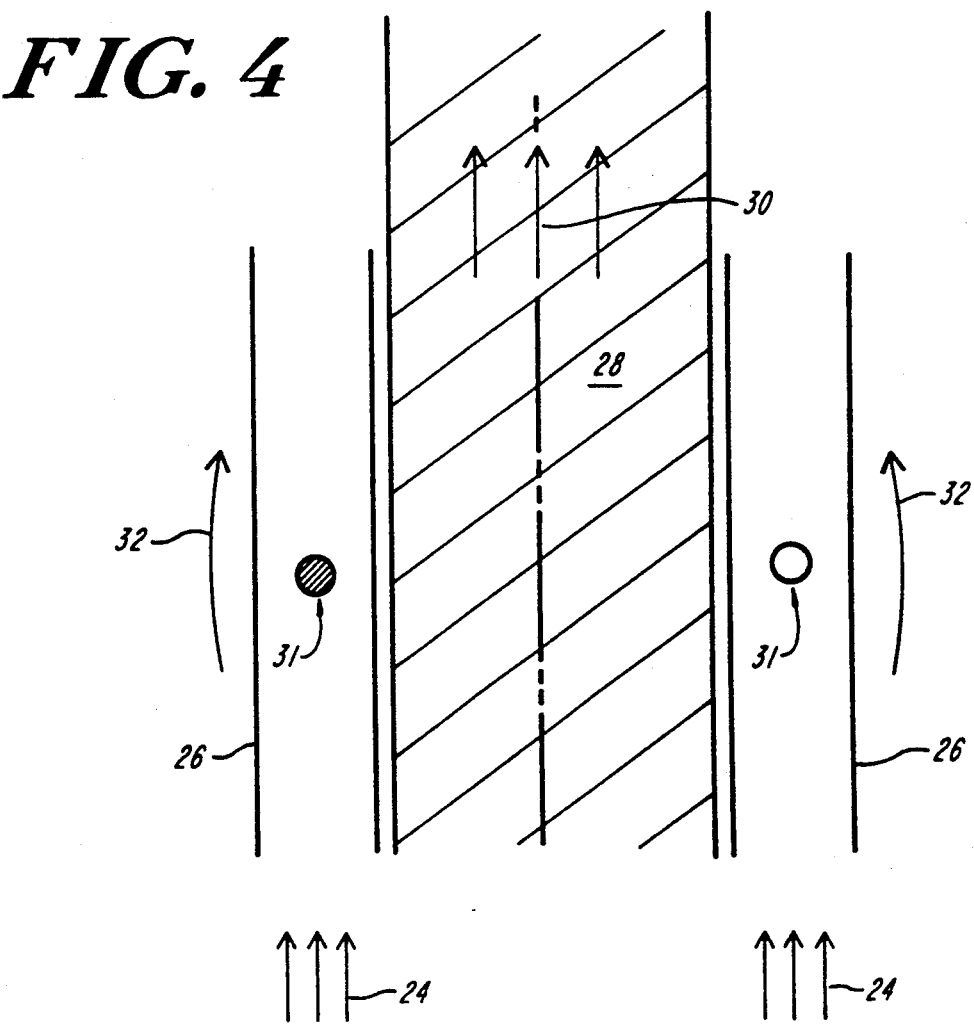

TUNABLE PLASMA METHOD AND APPARATUS USING RADIO FREQUENCY HEATING AND ELECTRON BEAM IRRADIATION

BACKGROUND OF THE INVENTION

This invention relates to systems for breaking down and synthesizing molecules, in particular to systems employing a tunable combination of radio frequency heating and electron beam irradiation.

In one aspect, the invention relates to systems for breaking down complex organic toxins. The use of electron beam irradiation to eliminate pollutants in smoke stack emissions is well-known. However, the use of electron beams to provide all the energy required is expensive and inflexible. Pure thermal plasma approaches wherein a plasma is created by heating a waste gas to a temperature sufficient to cause break-down of the molecules of the gas have been attempted. As an example, plasma torches have been used to destroy toxic wastes. A problem with such devices is that the electrodes degrade and must be replaced after repeated use. The use of electrodeless radio frequency-generated plasmas for toxic waste destruction at atmospheric pressures is limited by plasma stability and has not been employed in the field. Furthermore, both electrode and electrodeless thermal plasma approaches require higher temperatures (up to 20,000K) than are needed for optimum processing in many situations. These methods are expensive and inefficient since all molecules, even non-toxic components of the gas, are destroyed in the process.

SUMMARY OF THE INVENTION

In one aspect, the invention is a method for transferring energy to a gaseous medium by simultaneously coupling radio frequency energy to the gaseous medium and irradiating the gaseous medium with electron beam energy to create a plasma and to control the plasma chemistry. In one embodiment, the method is adapted for breaking down molecules, particularly complex organic toxins emanating from toxic wastes. Example toxins which can be destroyed using the invention are carbon tetrachloride, PCBs, nerve gas, and dioxin. In another embodiment, the method is adapted for the synthesis of molecules. The invention can be used, for example, to synthesize titanium oxide, a pigment in paint, as a particulate or aerosol. In yet another embodiment, the method is adapted for the creation of scavenger gases for destroying toxins or for sterilization procedures, for example. In another embodiment, the method is adapted to create a hot gas of large enthalpy for external materials processing and sterilization.

Other aspects of the invention are energy transfer apparatuses including a structure for containing a gaseous medium with means for transferring gases into and out of the structure, apparatus for coupling radio frequency energy to the gaseous medium, and apparatus for irradiating the gaseous medium with electron beam energy. The combination of radio frequency heating and electron beam irradiation creates a plasma and controls the chemistry of the plasma in the structure.

In some embodiments, radio frequency power is inductively coupled to the gas in the containing structure. In one example configuration, a coil encircling the containing structure is connected to a radio frequency power source for inductively heating the gas. In another configuration, the containing structure is annular and a radio frequency magnetic field is imposed in the core of said annular structure for inductively heating the gas.

In other embodiments, radio frequency power is coupled to the gas via waveguides and/or cavities. In one configuration, a radio frequency power source is connected by a conducting waveguide to a cavity adapted to couple the power to the gaseous medium. In another configuration, a radio frequency power source is connected to a conducting waveguide which is adapted to couple the power to the gas.

In preferred embodiments, the combination of radio frequency heating and electron beam irradiation is tunable, increasing the versatility of the method and apparatus. In one variation, the electron beam irradiation is used to ionize the gas and the radio frequency heating is used to drive selective chemical reactions at temperatures including those that are too low to sustain the plasma by radio frequency heating alone. In another variation, the electron beam irradiation is used to ionize the gas and to drive selective non-equilibrium chemical reactions and the radio frequency energy is used to tune the temperature of the gas to increase the efficiency of the chemical reactions. In a third variation, the radio frequency heating is used to ionize the gas and the electron beam irradiation is used to stabilize the plasma and to drive selective non-equilibrium chemical reactions.

In embodiments of the invention, a magnetic field is employed to affect the path of electrons in the electron beam irradiation. The magnetic field can be used to prevent electrons in the beam from striking the walls of a structure containing the gas. The magnetic field can further be used to control deposition of electrons in the beam so that the gas is uniformly affected by the electron beam irradiation, thus increasing electron beam efficiency.

A further embodiment of the invention is a two-chamber system for the destruction of toxic wastes. The first chamber heats solid or liquid wastes, preferably without the use of fossil fuels, to cause vaporization of toxic materials and the second chamber destroys the toxic gases using the tunable combination of inductive heating and electron beam irradiation. The second chamber can be, for example, any of the embodiments described above.

BRIEF DESCRIPTION OF THE DRAWING

FIG. 3 is a schematic illustration of one embodiment of apparatus according to the present invention, combining the configurations of FIGS. 1 and 2.

FIG. 4 is a schematic illustration of another embodiment of an apparatus for coupling radio frequency power to a gas using induction coils.

DESCRIPTION OF THE PREFERRED EMBODIMENT

Figure 1:
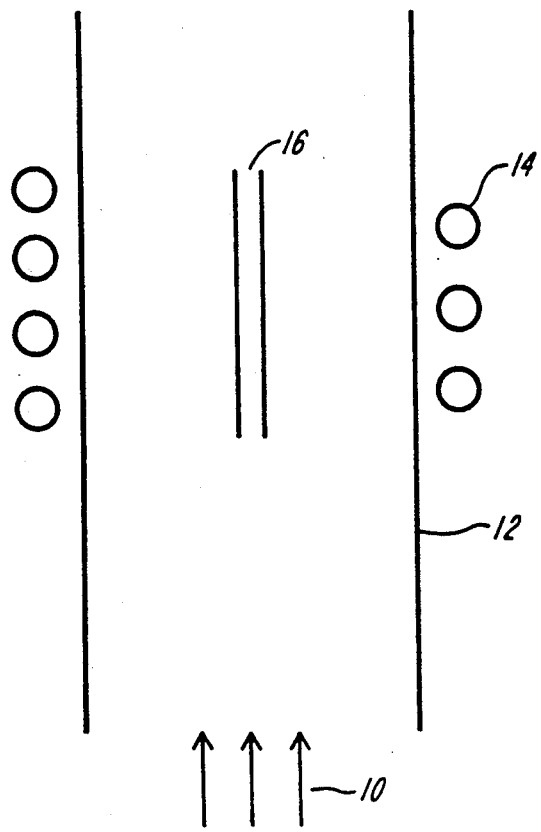
FIG. 1 is a schematic illustration of one embodiment of an apparatus for coupling radio frequency power to a gas using induction coils.

The present invention involves the use of an externally-driven radio frequency-heated plasma. By externally-driven it is meant that substantial ionization is provided by another source in addition to the radio frequency heating. In a particular embodiment, radio frequency power is delivered to the gas in the form of inductive discharges. Inductive discharges by themselves are very sensitive to the nature and properties of the gas, and if not controlled properly, they can contract or extinguish. It is necessary to have an externally-driven inductive discharge in order to make a robust system.

According to one aspect of the invention, an externally-generated electron beam is used to provide the ionized gas medium that is heated by the radio frequency energy. The electron beam provides stability in terms of both electrical and thermal avalanching. Only small amounts of electron beam power are required to control the heating characteristics of the plasma.

By varying the radio frequency heating and the electron beam powers it is possible to vary the nonthermal composition of the resulting plasma. Electron beams can be used to increase the density of the plasma, radicals, and excited atoms or molecules well beyond what is possible when the plasma is in thermal equilibrium. It is possible to make large densities of very reactive gases that, in conjunction with the additional radio frequency heating, can be used to break up molecules at relatively low temperatures.

Moreover, the use of the electron beam for ionization extends the operating temperature and pressure ranges of heated plasmas well beyond that possible with radio frequency heating alone, allowing operation at relatively low temperatures (as low as room temperature) and at pressures above atmospheric.

According to the invention, the combination of radio frequency heating and electron beam irradiation is tunable and the functions of the radio frequency heating and the electron beam are variable. In one variation, the primary function of the electron beam is to ionize the gas. The radio frequency power heats the ionized gas, thereby forming new products via high temperature reactions. The radio frequency power does not need to be high, as it does not have to produce electrons to sustain the plasma. Thus, selective chemical reactions can be driven at temperatures too low to sustain the plasma by radio frequency heating alone. In a second variation, radio frequency heating is used to tune the gas temperature to maximize the efficiency of chemical processes driven by highly reactive species generated by electron beam irradiation. In a third variation, the radio frequency heating ionizes the gas. The electron beam energy acts to stabilize the plasma and to create a large concentration of radicals and excited atoms and molecules in the radio frequency-produced plasma. These highly reactive species enhance the formation of new chemical products.

In all these cases, the resulting plasma is not purely thermal due to the presence of the electron beam. By adjusting the relative amount of radio frequency and electron beam power imparted to the gas, the chemistry of the plasma can be controlled. Further tuning can be accomplished by adjusting the energy of the electrons in the beam and the electron beam spatial distribution. Externally-applied magnetic fields can be used to control the trajectories of the electrons in the beam, as described in detail below. Tuning of the temperature is yet another way in which the present invention can be easily optimized and reoptimized for breaking down and synthesizing molecules of interest.

A further capability of the invention is the creation of scavenger gases. In one variation, the radio frequency energy is used to heat the gas, and the electron beam is used to create a non-equilibrium distribution of highly reactive species which can destroy toxic gases. For example, O and $O^+$ oxidize PCBs, and can also be used for sterilizing medical equipment and wastes.

The tunable system can also be used as a source of hot gas for various types of processing of external solids, liquids and gases, and for sterilization procedures.

Advantages of combining radio frequency heating with electron beam irradiation include the electrodeless operation, which removes the need for maintaining the electrodes and eliminates the electrode waste heat, decreasing downtime and increasing the efficiency of the burner. For synthesis applications, the absence of electrodes removes a source of contamination. Further, the power input can be varied at will by changing the radio frequency power or the electron beam power. The use of two power sources provides the control needed for reliable and efficient processing of a wide range of materials. The electron energy can be varied to accommodate different gas species. Large high temperature volumes, at high pressures, can be created, with good uniformity. Limits on heating volume in pure radio frequency discharges due to skin depth effects can be greatly alleviated. Additional control of the temperature/density of the plasma is provided, making possible operation with non-thermal plasmas; the electron beams can be used to facilitate certain chemical reactions by producing selective reactive species.

In one embodiment of the invention, an inductively coupled radio frequency discharge is applied to a gas using the arrangement shown in FIG. 1. As indicated, a gas 10 flows through a chamber 12 around which coupling coils 14 are wrapped. The chamber is preferably made out of a non-conducting material such as quartz. The partially conducting gas acts as the secondary of a transformer. A time-varying current through the coils imparts energy to the gas, resulting in the linear plasma 16. In this embodiment, the time-varying current is preferably a sinusoid at frequencies between 60 Hz and 100 MHz. The approach can also be extended to higher frequencies by use of cavities and waveguides to couple electromagnetic energy to the conducting gas, an embodiment described in detail below.

Figure 2:
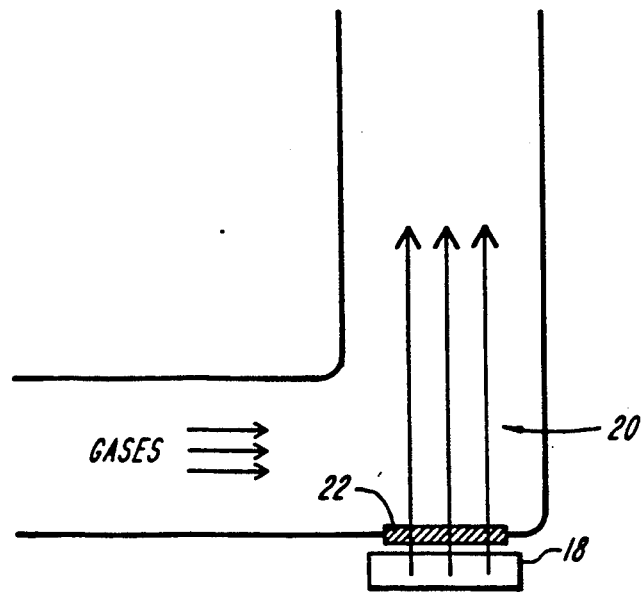
FIG. 2 is a schematic illustration of one embodiment of an apparatus for irradiating a gas with an electron beam.

The electron beam can be applied to the gas using, for example, the configuration shown in FIG. 2. As shown, an electron beam generator 18 is configured to transmit the electron beam 20 through the window 22.

A system combining the inductive discharge and electron beam configurations of FIGS. 1 and 2 is illustrated in FIG. 3.

The inductive discharge can also be applied using the configuration shown in FIG. 4. In this embodiment, a gas 24 flows through an annular chamber 26. The chamber is preferably made out of a non-conducting material such as quartz. The core of the annular chamber is filled with a material of high permeability 28, such as soft iron. A time varying magnetic field 30 induces a toroidal plasma 31 which is held in a stable position along the length of the chamber by the external field 32.

Figure 5:
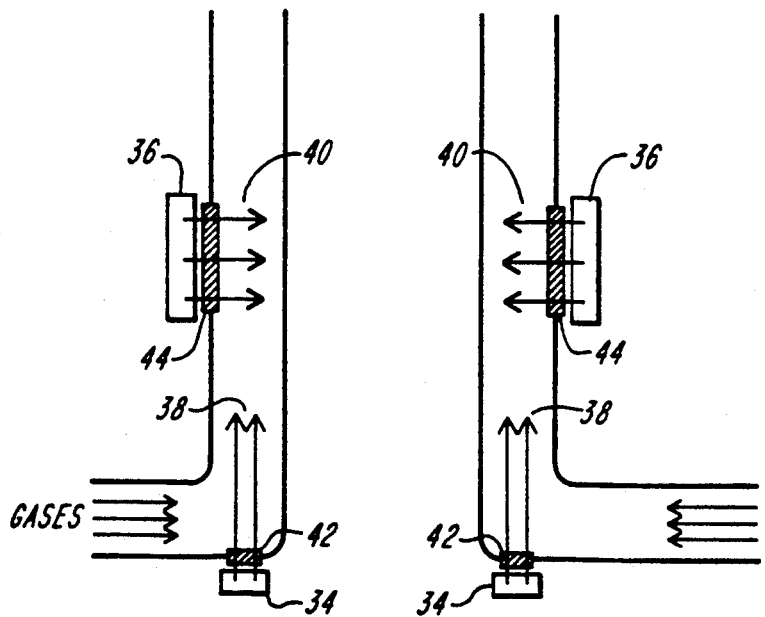
FIG. 5 is a schematic illustration of another embodiment of an apparatus for irradiating a gas with an electron beam.

The electron beam can be applied to the gas using one or both of the configurations shown in FIG. 5. As shown, electron beam generators 34 and 36 are configured to transmit electron beams 38 and 40 through the windows 42 and 44. A linear arrangement of electron beam generators, rather than point sources, is recommended. Preferably, the generators 34 and 36 form continuous annuli around the chamber.

Figure 6:
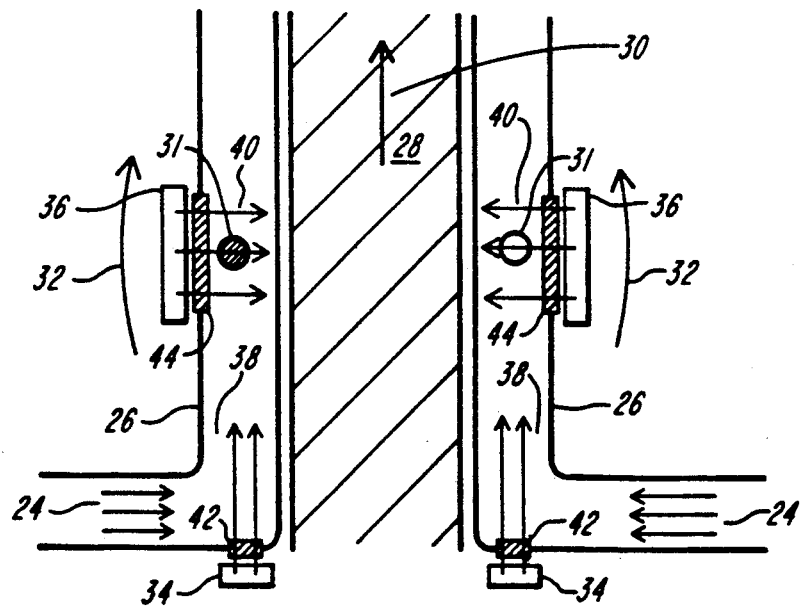
FIG. 6 is a schematic illustration of another embodiment of apparatus according to the present invention, combining the configurations of FIGS. 4 and 5.

A system combining an inductive heating and electron beam configurations of FIGS. 4 and 5 is illustrated in FIG. 6. It will be recognized by those skilled in the art that other configurations combining inductive heating and electron beam irradiation, beyond those illustrated in FIGS. 3 and 6, are within the scope of the invention.

For pure inductive heating in the kilohertz to 100 megahertz range, the skin depth becomes an issue. If the frequency is too low, the coupling will not be adequate; if the frequency is too high, too much energy will be in the skin. Further, tunable radio frequency sources are expensive. However, the tunability provided by the use of the electron beam allows the use of a single frequency radio frequency source for a variety of gases by matching the skin depth of the electron-beam produced plasma to the radio frequency source.

Figure 7:
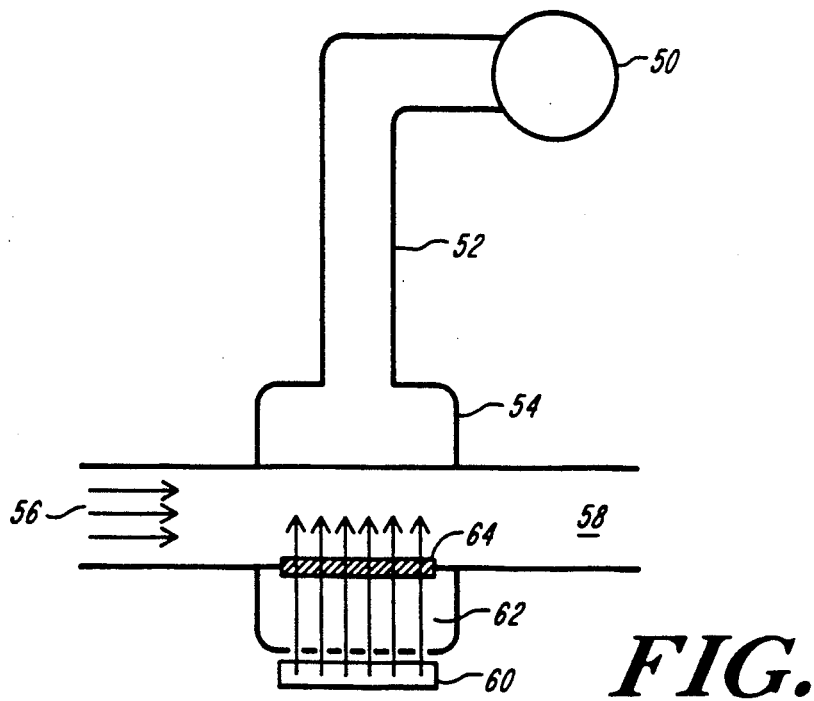
FIG. 7 is a schematic illustration of one embodiment of apparatus for coupling radio frequency power to a gas under electron beam irradiation with a waveguide/cavity configuration.

The method of the invention can be extended to higher frequencies (up to about 3000 MHz using currently practical sources of radio frequency power) by use of cavities and waveguides to couple electromagnetic energy to the gas. FIG. 7 illustrates an embodiment of the present invention which employs a conducting waveguide and cavity to couple electromagnetic power to the electron beam-driven conducting gas. As indicated, the radio frequency power is provided by a high power tube 50 and travels as an electromagnetic wave through a waveguide 52 into a cavity 54. The cavity and the waveguide are designed to optimize coupling of the power to a gas 56 in a non-conducting chamber 58. In preferred embodiments, the waveguide 52 and the cavity 54 are made of copper, and the chamber 58 is made of quartz. As in the previous embodiments, an electron beam generator or generators 60 is configured to transmit an electron beam or beams 62 through the window or windows 64.

Figure 8:
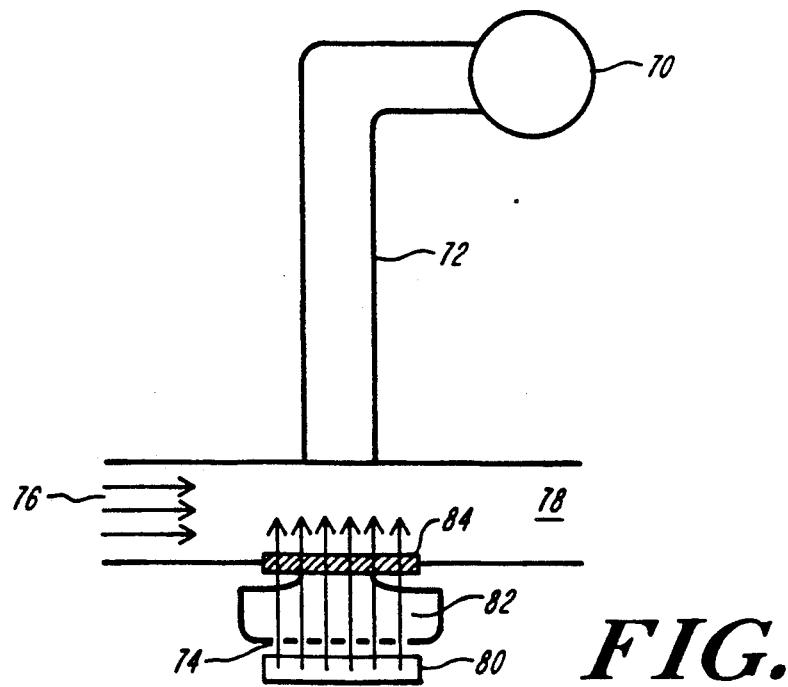
FIG. 8 is a schematic illustration of one embodiment of apparatus for coupling radio frequency power to a gas under electron beam irradiation with a waveguide.

In a variation of this embodiment, the radio frequency power is coupled to the gas by the waveguide alone, as illustrated in FIG. 8. As shown, the radio frequency power is provided by a high power tube 70 and travels as an electromagnetic wave through a waveguide 72 to a dump 74. The waveguide is designed to optimize coupling of the power to the gas 76 in the non-conducting chamber 78. In preferred embodiments, the waveguide 72 is made of copper, and the chamber 78 is made of quartz. An electron beam generator or generators 80 is configured to transmit an electron beam or beams 82 through the window or windows 84.

In all of the embodiments described above, the energy of the electrons in the electron beam is determined by the size of the chamber, the pressure, and to a lesser degree, the nature of the gas. Energies between 100–500 keV are appropriate and are preferably selected to provide adequate penetration. The mean free path of the electron beam is preferably comparable to or smaller than the size of the chamber, in order to prevent large shine-through. The mean free path should also not be much smaller than the chamber size, because the electron beam deposition will not be uniform. The ratio of the electron mean free path in the gas at the injection energy and the effective size of the chamber is preferably between two and six.

The electron current that can be extracted through a window is about 1 mA/cm in a linear beam configuration. Assuming 200 keV electron beam energy, then the power per unit beam width is 200 W/cm. The beam injection units can be stacked next to each other to increase the total power per unit length.

In order to increase the efficiency of the system, and to protect as much as possible the electron beam window, it is desirable to operate at low temperature. The temperature of the gas operation is preferably 1000°–4000° C. The required power levels depend upon the flow rate of the gas. Typical power levels are about 100 kW for 10 tons/day of throughput.

Figure 9:
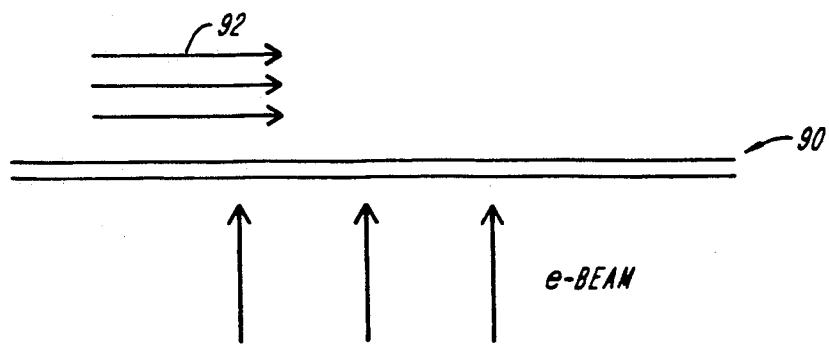
FIG. 9 is a schematic illustration of the electron beam window of the present invention.

The window of the electron beam injector is subjected to the damaging action of the beam itself and the corrosive environments in the chamber. As shown in FIG. 9, one way to minimize the damage is to protect the window 90 by a slow flow of gas 92 (such as nitrogen) in the area near the window.

Another way to minimize window damage is to fabricate the window of materials that are resistant to corrosion, such as thin films made of materials such as diamond or diamond-like film, silicon carbide, boron nitride, aluminum oxide, or silicon nitride. these films are easy to manufacture and can be supported against the atmospheric load by a grid or mesh. The grid or mesh can be made either separate from the film, or as an integrated part of the film by growing the film on a substrate and then etching away most of the substrate material. The remaining substrate material will provide the required support and cooling. The advantages of diamond and diamond-like carbon films are their very large thermal conductivity, high resistance to corrosion, very large strength, and low interception of the electron beam resulting in low window heating. Silicon carbide, boron nitride, aluminum oxide, and silicon nitride share these properties (with the exception of the high thermal conductivity) but have the advantage of good high-temperature properties.

Applied magnetic fields of different magnitudes can be used to modify the electron beam path for optimum operation. This adds yet another tuning mechanism. An applied magnetic field can be used to prevent electrons from reaching the walls, thus minimizing shine-through. This is especially important when high energy electron beams are used which might hit the other side of the chamber, creating x-rays. This mechanism also can be used to control the deposition of the electrons to ensure that the gas is uniformly affected by the electron beam. The magnetic field is preferably constant or very slowly time-varying (with period on the order of seconds). The magnitude of the magnetic field can be varied to allow optimum use of electron beams of varying energy.

Figure 10:
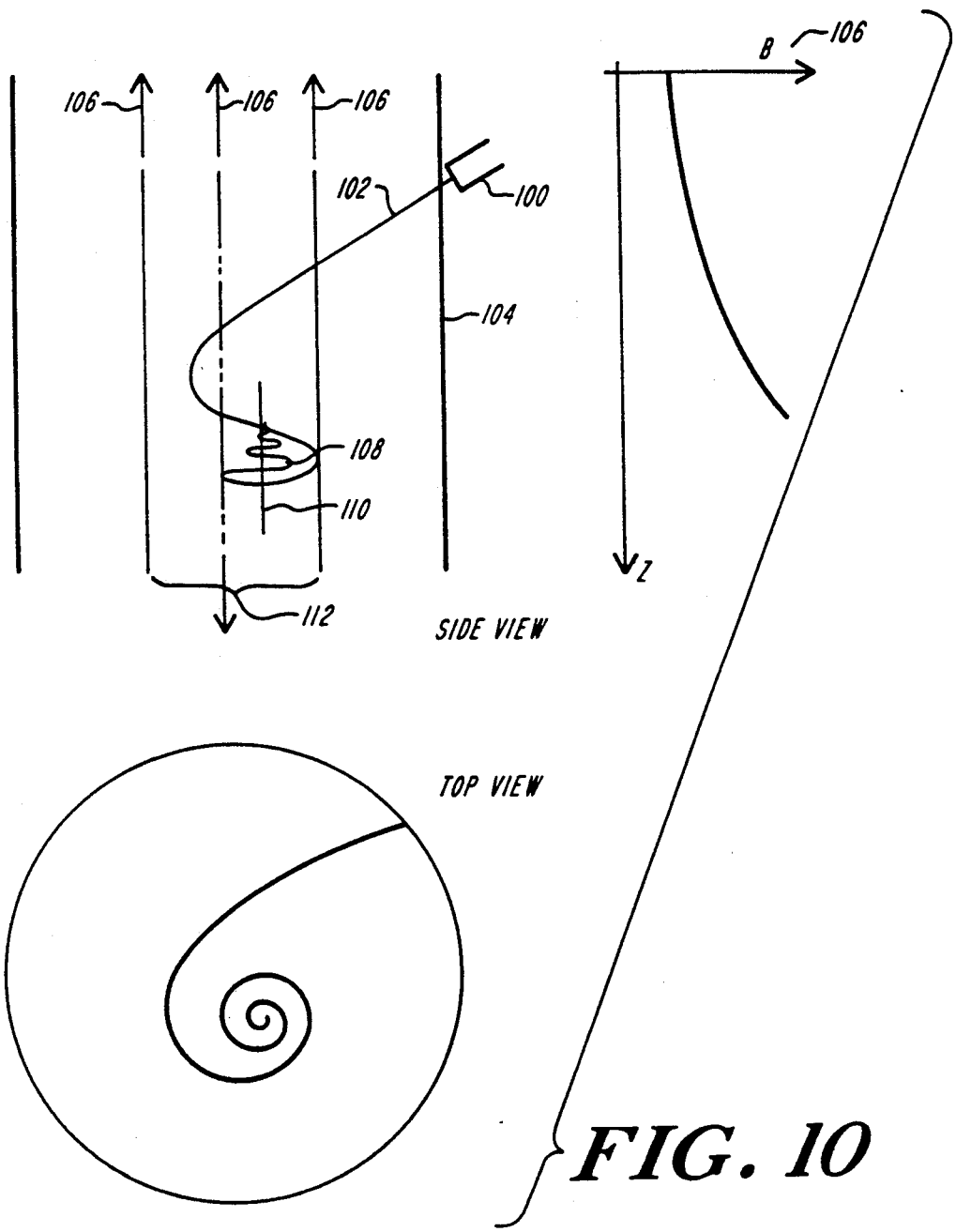
FIG. 10 is a diagram showing the effect of an imposed magnetic field on the electron beam trajectory for a magnetic field perpendicular to the electron beam path.

One use of magnetic fields to alter the paths of electrons is illustrated in FIG. 10. In this embodiment, the magnetic field direction is roughly perpendicular to path of the electrons. As shown, an electron source 100 injects electrons 102 into the chamber 104. A magnetic field 106, having the dependence on height shown in the figure, is applied inside the chamber. As the electrons slow down, the magnetic forces change the direction of the motion in a spiral-like pattern 108 with an axis 110 inside the plasma 112. The electrons spin while slowing down until they have lost all their energy. Low values of magnetic field are required. As the motion of an electron in a magnetic field depends on its energy, tuning of the electron beam energy and the magnetic field strength in tandem can be used to obtain the desired spatial electron deposition. At 100 G, the gyro radius of a 500 keV electron is about 10 cm.

Figure 11:
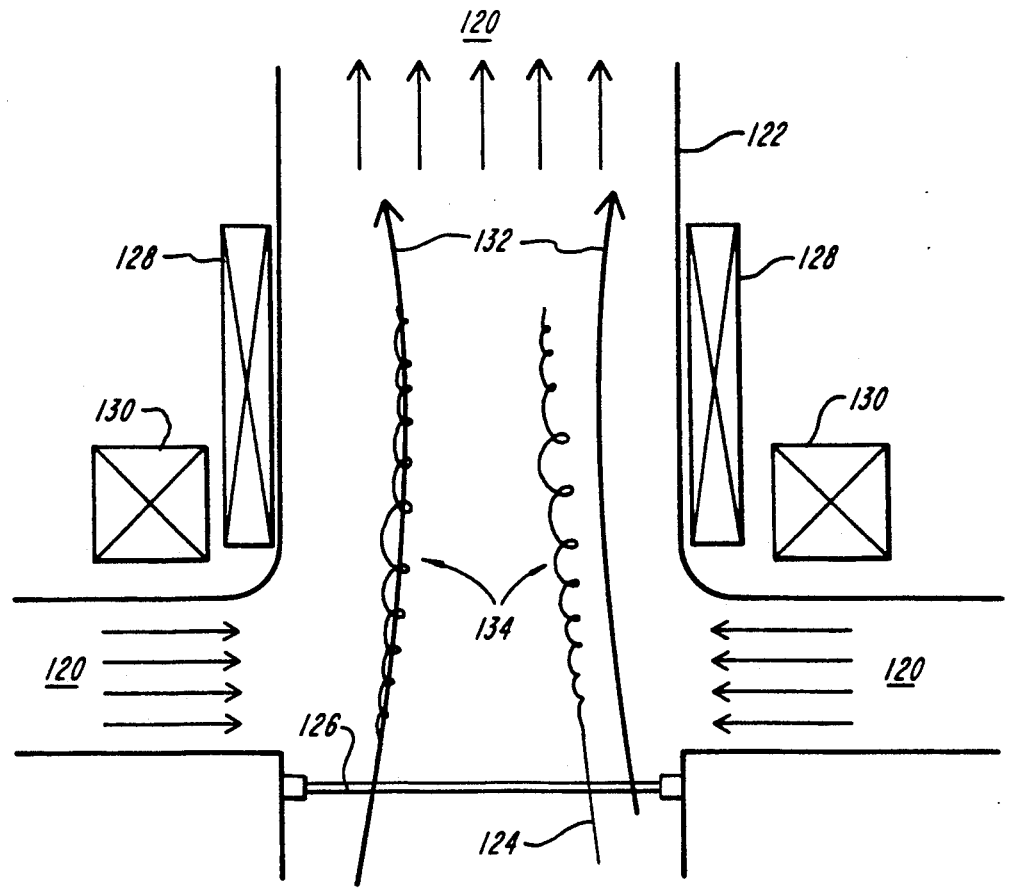
FIG. 11 is a schematic illustration of one embodiment of apparatus for altering electron beam trajectory with application of a magnetic field parallel to the electron beam path and to the gas flow.

In an alternative embodiment, a magnetic field parallel to the direction of electron beam injection is used to prevent electrons from striking the side walls and producing large amounts of x-rays. An embodiment where the electron beam path and the magnetic field are parallel to the gas flow is illustrated in FIG. 11. As shown, gases 120 enter the chamber 122 and flow in an upward direction. Electrons 124 are injected in an upward direction through the window 126. Induction coils 128 provide the inductive heating. A second coil 130 provides the magnetic field 132 having an upward direction. This applied magnetic field acts to prevent scattering of the electrons, keeping them on an upward path 134 and away from the walls of the chamber. Magnetic fields on the order of 1 kilogauss (corresponding to Larmor radius or ~1 cm for ~100 KeV electrons) are appropriate for this embodiment.

Figure 12:
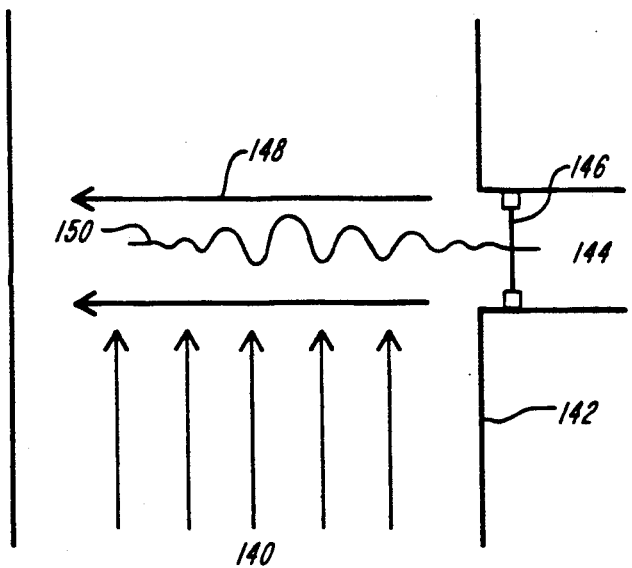
FIG. 12 is a schematic illustration of one embodiment of apparatus for altering electron beam trajectory with application of a magnetic field parallel to the electron beam path but perpendicular to the gas flow.

An embodiment where the electron beam path and the magnetic field are perpendicular to the gas flow is illustrated in FIG. 12. As shown, gases 140 flow upward in the chamber 142. Electrons 144 are injected perpendicular to the flow through the window 146. An applied magnetic field 148 parallel to the path 150 of the electrons acts to prevent scattering.

Figure 13:
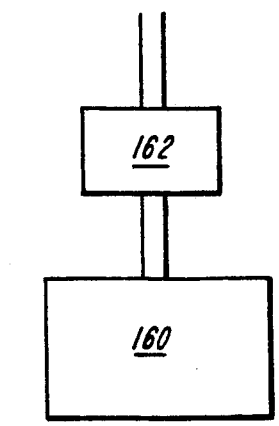
FIG. 13 is a schematic illustration of a two-chamber system according to the present invention.

A two chamber system for the destruction of wastes according to the present invention is shown in FIG. 13. The first chamber 160 heats the solid/liquid wastes, which may not be well characterized, and the second chamber 162 destroys the toxic gases generated by the heating of the material. The second chamber uses the combined radio frequency-electron beam system described above. The secondary system can be, for example, one of the embodiments illustrated in FIGS. 3, 6, 7, or 8, optionally employing an imposed magnetic field as in FIGS. 10-12.

The purpose of the first chamber is to heat the solids and/or liquids to temperatures such that the organic contaminants vaporize, leaving a sludge composed of metals and inorganic materials. This sludge can be allowed to solidify in a separate chamber, immobilizing the heavy metals. The temperature of the first chamber preferably should be sufficiently high to vaporize all toxic organic materials in the mixed waste (so that all toxins can be treated in the secondary chamber) and to melt the solids (so that the non-volatile toxic metals become immobilized after the slag solidifies).

Ideally, the heating of the solid/liquid wastes in the first chamber should be done without the use of fossil fuels that would increase the gas loading of the secondary chamber. Any of a large number of methods can be used, such as an electric discharge operating with electrodes (arc, torch), inductively heated plasmas at AC frequencies, or radio frequency heating.

The advantages of using plasmas or radio frequency heating for the primary combustion chamber include the absence of the burning of fossil fuels which minimizes the gas throughput in the secondary chamber and in the gas treatment system following the secondary chamber. Further, in comparison to incinerators, relatively small size units are possible. With the present invention, power input can be varied widely in short periods of time, including fast turn-on and shut-down phases. The temperature of the solid and liquid waste can be adjusted by controlling the power in the first chamber.

As discussed above, systems for waste destruction employing electron beam irradiation or pure thermal plasmas have been developed in the past. The details of the physical embodiments and the use of these units are relevant to aspects of the present invention. The following articles, herein incorporated by reference, describe existing plasma arc and electron beam units.

"High-power selfshielded electron processors and their application to stack gas treatment" by J. Hiley et al., in *Nuclear Instruments and Methods in Physics Research*, B24/25, pp. 985-989, 1987.

"Operating and testing a combined $SO_2$ and $NO_x$ removal facility" by N. W. Frank et al., in *Environmental Progress*, Vol. 6, pp. 177-182, August 1987.

"Stack testing of the mobile plasma arc unit" by M. Gollands et al., in *EPA Project Summary*, EPA/600/S2-87/013 May 1987.

"Trial burns-plasma arc technology" by N. P. Kolak et al., in *Nuclear and Chemical Waste Management*, Vol. 7, pp. 37-41, 1987.

It is recognized that modifications and variations of the invention will occur to those skilled in the art, and it is intended that all such modifications and variations be within the scope of the claims.

What is claimed is:

1. Method for energy transfer to a gaseous medium comprising simultaneously and continuously coupling radio frequency energy to the gaseous medium and irradiating the gaseous medium with electron beam energy, whereby a simultaneous and continuous combination of radio frequency heating and electron beam irradiation creates a plasma and controls plasma chemistry.

2. The method of claim 1 wherein the simultaneous and continuous combination of radio frequency heating and electron beam irradiation is tunable, thereby allowing variable control of plasma temperatures.

3. The method of claim 1 wherein the gaseous medium comprises toxic molecules and wherein the simultaneous and continuous combination of radio frequency heating and electron beam irradiation is adapted to destroy said molecules.

4. The method of claim 1 wherein the simultaneous and continuous combination of radio frequency heating and electron beam frequency irradiation is adapted to synthesize new molecules from the molecules of the gaseous medium.

5. The method of claim 1 wherein the simultaneous and continuous combination of radio frequency heating and electron beam irradiation is adapted to create a hot gas with large enthalpy for use outside a structure containing the hot gas.

6. The method of claim 5 wherein the hot gas is used for materials processing at no less than atmospheric pressure.

7. The method of claim 5 wherein the hot gas is used for sterilization procedures.

8. The method of claim 1 wherein the simultaneous and continuous combination of radio frequency heating and electron beam irradiation is adapted to create a non-equilibrium distribution of highly reactive species.

9. The method of claim 8 wherein the highly reactive species is used for sterilization procedures.

10. The method of claim 1 wherein the electron beam irradiation is adapted to ionize the gaseous medium and the radio frequency heating is adapted to drive selective chemical reactions at temperatures lower than those required to sustain the plasma by radio frequency heating alone.

11. The method of claim 1 wherein the electron beam irradiation is adapted to ionize the gaseous medium and to drive selective non-equilibrium chemical reactions, and the radio frequency heating is adapted to tune the temperature of the gaseous medium to increase chemical reaction efficiency.

12. The method of claim 1 wherein the radio frequency heating is adapted to ionize the gaseous medium and the electron beam irradiation is adapted to stabilize the plasma and to drive selective non-equilibrium chemical reactions.

13. The method of claim 1 further comprising applying a magnetic field to the gaseous medium to affect the path of electrons in said electron beam irradiation.

14. A two-chamber system for destroying toxic waste comprising a first chamber adapted to heat and vaporize said toxic waste and a second chamber adapted to receive gases from said first chamber and to break down toxic molecules in the gases via a tunable combination of simultaneous and continuous inductive heating and electron beam irradiation at no less than atmospheric pressure and at temperatures lower than those required to destroy toxic waste by inductive heating alone.

15. The two-chamber system of claim 14 wherein said second chamber comprises:

a structure for containing a gaseous medium including an apparatus for transferring gases in and out of said structure, a first apparatus for coupling radio frequency energy to the gaseous medium, and a second apparatus for irradiating the gaseous medium with electron beam energy, whereby a simultaneous and continuous combination of radio frequency heating and electron beam irradiation creates a plasma and controls plasma chemistry.

16. The two-chamber system of claim 15 wherein said first apparatus for coupling radio frequency energy to the gaseous medium comprises induction coils encircling said structure connected to a radio frequency power source for inductively heating the gaseous medium.

17. The two-chamber system of claim 15 wherein said structure is annular and wherein said first apparatus for coupling radio frequency energy to the gaseous medium comprises induction coils connected to a radio frequency power source adapted to impose a radio frequency magnetic field in the core of said annular structure for inductively heating the gaseous medium.

18. The two-chamber system of claim 15 wherein said first apparatus for coupling radio frequency energy to the gaseous medium comprises a radio frequency power source connected by a conducting waveguide of electromagnetic radiation to a cavity adapted to couple said radio frequency power to the gaseous medium.

19. The two-chamber system of claim 15 wherein said first apparatus for coupling radio frequency energy to the gaseous medium comprises a radio frequency power source connected by a conducting waveguide of electromagnetic radiation adapted to couple said radio frequency power to the gaseous medium.

20. Method for energy transfer to a gaseous medium comprising simultaneously and continuously coupling radio frequency energy to the gaseous medium and irradiating the gaseous medium with electron beam energy, at no less than atmospheric pressure, whereby a simultaneous and continuous combination of radio frequency heating and electron beam irradiation creates a plasma and controls plasma chemistry.

* * * * *